(12) United States Patent
Killion et al.

(10) Patent No.: US 9,867,572 B2
(45) Date of Patent: Jan. 16, 2018

(54) METHOD AND SYSTEM FOR RAPIDLY DETERMINING AND DISPLAYING THE DEPTH OF EAR TIP PLACEMENT TO IMPROVE THE RELIABILITY OF HEARING TESTS

(71) Applicant: Etymotic Research, Inc., Elk Grove Village, IL (US)

(72) Inventors: Mead Killion, Elk Grove Village, IL (US); Jonathan Siegel, Skokie, IL (US); Sumitrajit Dhar, Wilmette, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 618 days.

(21) Appl. No.: 14/483,109

(22) Filed: Sep. 10, 2014

(65) Prior Publication Data

US 2015/0073297 A1 Mar. 12, 2015

Related U.S. Application Data

(60) Provisional application No. 61/875,769, filed on Sep. 10, 2013.

(51) Int. Cl.
*A61B 5/00* (2006.01)
*A61B 5/12* (2006.01)

(52) U.S. Cl.
CPC ............ *A61B 5/6844* (2013.01); *A61B 5/126* (2013.01); *A61B 5/6817* (2013.01); *A61B 5/742* (2013.01); *A61B 5/7278* (2013.01)

(58) Field of Classification Search
CPC ..... A61B 5/6844; A61B 5/126; A61B 5/6817; A61B 5/742; A61B 5/7278; A61B 7/04; A61B 5/7282
See application file for complete search history.

(56) References Cited

U.S. PATENT DOCUMENTS

| 4,852,683 A * | 8/1989 | Killion ..................... A61F 11/10 |
| | | 181/130 |
| 2008/0144864 A1* | 6/2008 | Huon ....................... H04R 1/20 |
| | | 381/305 |

(Continued)

OTHER PUBLICATIONS

J. Lee et al., Behavioral Hearing Thresholds Between 0.125 and 20kHz Using Depth-Compensated Ear Simulator Calibration, Ear & Hearing, vol. 33, No. 1, 00-00, 2012.

(Continued)

*Primary Examiner* — Sean Dougherty
(74) *Attorney, Agent, or Firm* — McAndrews, Held & Malloy, Ltd.

(57) ABSTRACT

Methods and systems for rapidly determining and displaying the depth of ear tip placement to improve the reliability of hearing tests may comprise in a hearing assessment system comprising a control system and a probe with a sealing ear tip, a microphone, and a sound source: measuring a pressure versus frequency of an ear canal, determining a first half-wavelength frequency of the ear canal using the measured pressure versus frequency and/or or from the phase of the ear canal reflectance, and calculating a distance between the hearing probe and an eardrum in the ear canal based on the determined first half-wavelength frequency. Subsequent measurements of the ear canal may be performed using the calculated distance. The calculated distance may be stored in a memory in the control system for the subsequent measurements of the ear canal. The calculated distance may be displayed on a gauge on the control system.

20 Claims, 9 Drawing Sheets

(56) References Cited

U.S. PATENT DOCUMENTS

2011/0009770 A1\* 1/2011 Margolis ................ A61B 5/121
 600/559
2012/0283593 A1\* 11/2012 Searchfield ........... A61M 21/00
 600/559
2016/0372104 A1\* 12/2016 Nystrom ............ G10K 11/1784

OTHER PUBLICATIONS

Souza et al., "Comparison of Nine Methdos to Estimate Ear-Canal Stimulus Levels", J. Acoustical Society of America, vol. 136, No. 4 Oct. 2014.

\* cited by examiner

METHOD AND SYSTEM FOR RAPIDLY DETERMINING AND DISPLAYING THE DEPTH OF EAR TIP PLACEMENT TO IMPROVE THE RELIABILITY OF HEARING TESTS

CROSS-REFERENCE TO RELATED APPLICATIONS/INCORPORATION BY REFERENCE

This application makes reference to and claims priority to United States Provisional Application Ser. No. 61/875,769 filed on Sep. 10, 2013. The above identified application is hereby incorporated herein by reference in its entirety.

FEDERALLY FUNDED RESEARCH AND DEVELOPMENT

This invention was made with government support under contract number N00014-12-C-01087 awarded by the Office of Naval Research. The government has certain rights in the invention.

FIELD

Certain embodiments of the invention relate to audio sensors. More specifically, certain embodiments of the invention relate to a method and system for rapidly determining and displaying the depth of ear tip placement to improve the reliability of hearing tests.

BACKGROUND

Hearing loss due to excessive sound intensities is common in modern society, especially in people whose occupations subject them to such high sound levels. For example, one third of warfighters return from active duty with hearing loss. Not only does this hearing loss impair function after returning home, it can put them at risk during active duty, as hearing can be even more important than eyesight when detecting enemy personnel on patrol. It can also put his fellow warfighters at risk, as military personnel depend on each other to avoid unnecessary danger. Accurate and effective hearing testing is therefore extremely important.

Further limitations and disadvantages of conventional and traditional approaches will become apparent to one of skill in the art, through comparison of such systems with the present invention as set forth in the remainder of the present application with reference to the drawings.

BRIEF SUMMARY

A system and/or method for rapidly determining and displaying the depth of ear tip placement to improve the reliability of hearing tests substantially as shown in and/or described in connection with at least one of the figures, as set forth more completely in the claims.

Various advantages, aspects and novel features of the present invention, as well as details of an illustrated embodiment thereof, will be more fully understood from the following description and drawings.

DETAILED DESCRIPTION

Certain aspects of the disclosure may be found in a method and system for rapidly determining and displaying the depth of ear tip placement to improve the reliability of hearing tests. Exemplary aspects of the invention may comprise, in a hearing assessment system comprising a control system and a probe with a sealing ear tip, a microphone, and a sound source: measuring a pressure versus frequency of an ear canal, determining a first half-wavelength frequency of the ear canal using the measured pressure versus frequency, and calculating a distance between the hearing probe and an eardrum in the ear canal based on the determined first half-wavelength frequency. Subsequent measurements of the ear canal may be performed using the calculated distance. The calculated distance may be stored in a memory in the control system for the subsequent measurements of the ear canal. The calculated distance may be displayed on a gauge on the control system. The distance between the hearing probe and the eardrum in the ear canal may also be estimated from the phase vs. frequency of the reflectance of the ear canal. Either or both of the half-wave or phase method may be used to provide the display of estimated distance. Other means such as optical measurements can be used independently or combined for greater accuracy.

As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the terms "block" and "module" refer to functions than can be implemented in hardware, software, firmware, or any combination of one or more thereof. As utilized herein, the term "exemplary" means serving as a non-limiting example, instance, or illustration. As utilized herein, the term "e.g.," introduces a list of one or more non-limiting examples, instances, or illustrations.

Figure 1:
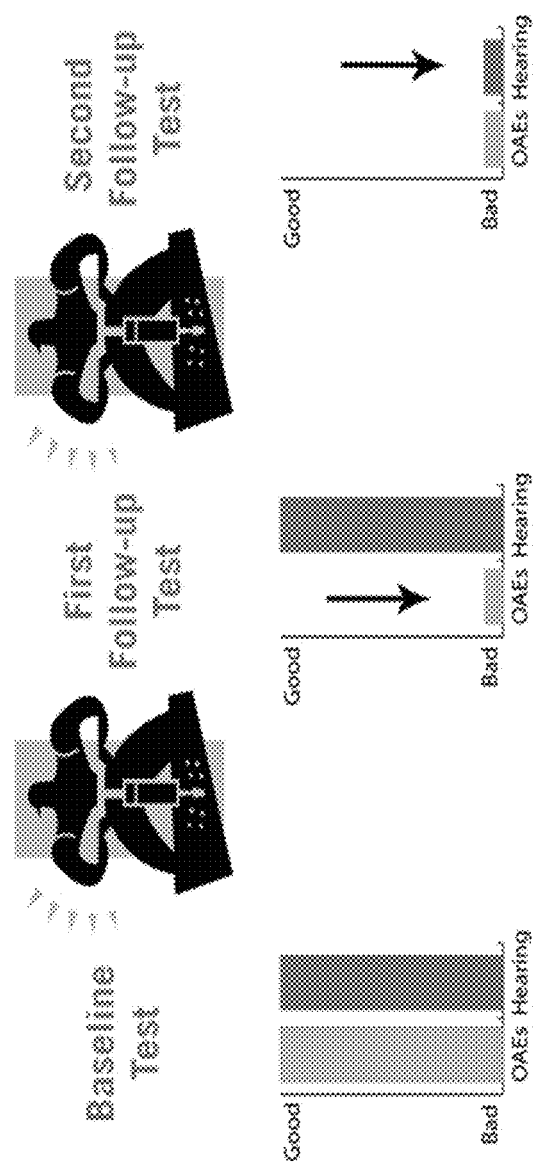
FIG. 1 illustrates the benefit of measuring otoacoustic emissions in providing an advance warning of impending permanent hearing loss in persons exposed to excessive sound levels.

FIG. 1 illustrates the benefit of measuring otoacoustic emissions in providing an advance warning of impending permanent hearing loss in persons exposed to excessive sound levels. The work described here was motivated by reports that the level of the otoacoustic emission (OAE) from the ear often started to drop with noise exposure before a noticeable hearing loss appeared. Marshall, et al. (2009)

reported that " . . . the increased sensitivity of OAEs in comparison to audiometric thresholds was shown in all analyses, and low-level OAEs indicate an increased risk of future hearing loss by as much as nine fold. (Marshall L, Lapsley Miller J A, Heller L M, Wolgemuth K S, Hughes L M, Smith S D and Kopke R D (2009). Detecting incipient inner-ear damage from impulse noise with otoacoustic emissions. *Journal of the Acoustical Society of America* Vol. 125, No. 2, pp. 995-1013.) This followed an earlier report that permanent hearing loss was predicted by low-level or absent otoacoustic emissions, with risk increasing more than six fold as the emission amplitude decreased. (Lapsley Miller J A, Marshall L, Heller L M, and Hughes L M (2006). *Journal of the Acoustical Society of America* Vol. 120, No. 1, pp. 280-296.) This finding was illustrated by Marshall in the Cartoon example, as shown in FIG. 1.

In typical OAE measurements, two tones are applied to the eardrum having frequencies F1 and F2 with a typical frequency ratio of 1.22:1. For example, F1 at 65 dB sound pressure level (SPL) at a frequency of 4 kHz and F2 at 55 dB SPL at a frequency of 5 kHz will, in a healthy ear, result in an OAE tone generated by the distortion in the outer hair cells in the cochlea at a frequency of 2F1-F2, in this case 3 kHz. The level of that tone in the ear canal can be 10 to 20 dB SPL in a young child to typically –10 dB to 10 dB SPL in an adult.

The problem in applying the Marshall finding has been that the test-retest variability of both subjective hearing threshold and objective OAE measurements are often so large as to make it difficult to detect the warning signs in individual cases.

Figure 2A:
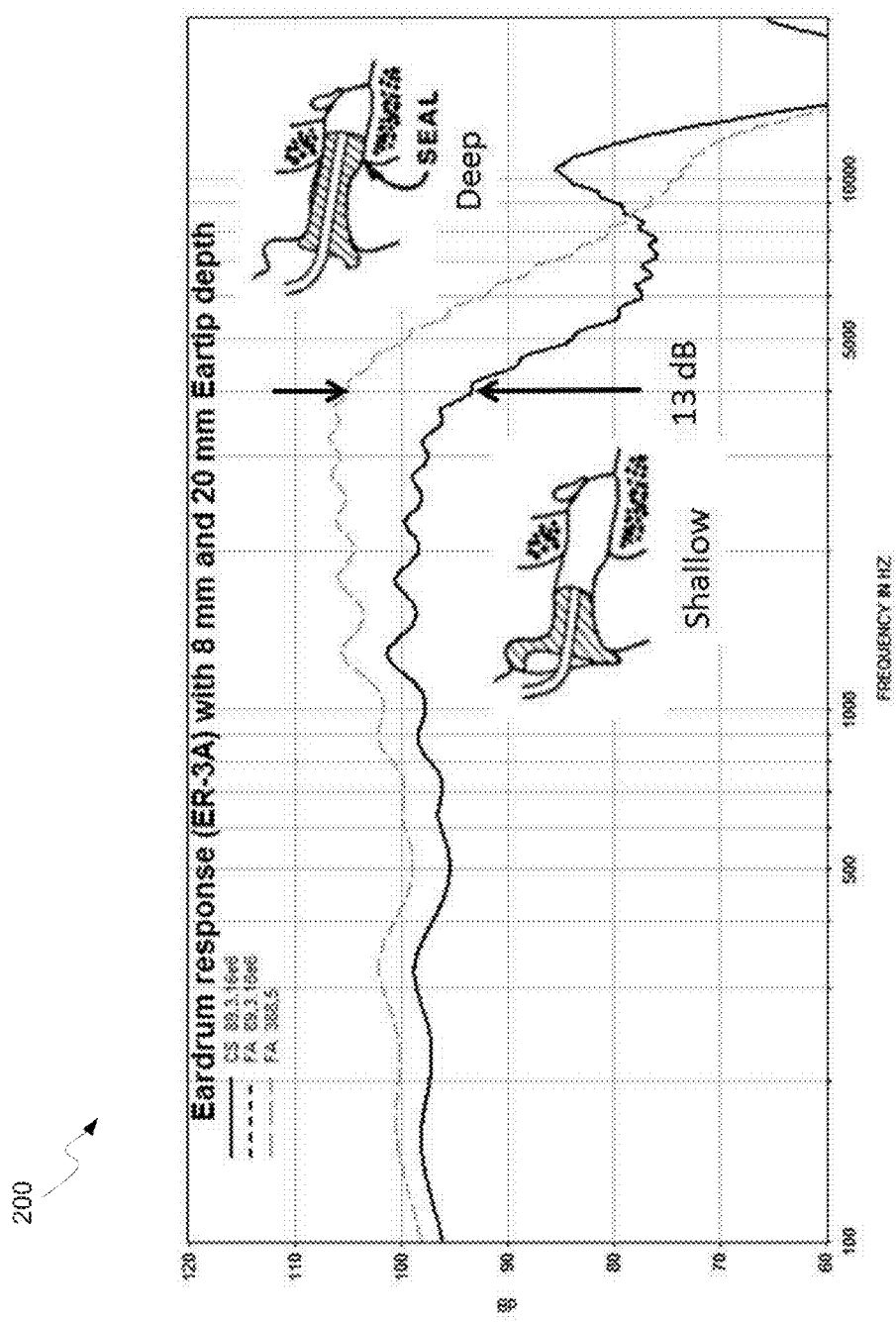
FIG. 2A is a graph of calculated eardrum response versus frequency for two different ear tip depths.

FIG. 2A is a graph of eardrum response versus frequency for different ear tip depth, illustrating part of the problem. Referring to FIG. 2A, there is shown a calculated plot 200 of typical eardrum response for two ear tip placements, the top one being deeper at 20 mm, and the bottom curve illustrating eardrum response for an 8 mm depth. The different depths may result in a 13 dB difference at 4 kHz.

Figure 2B:
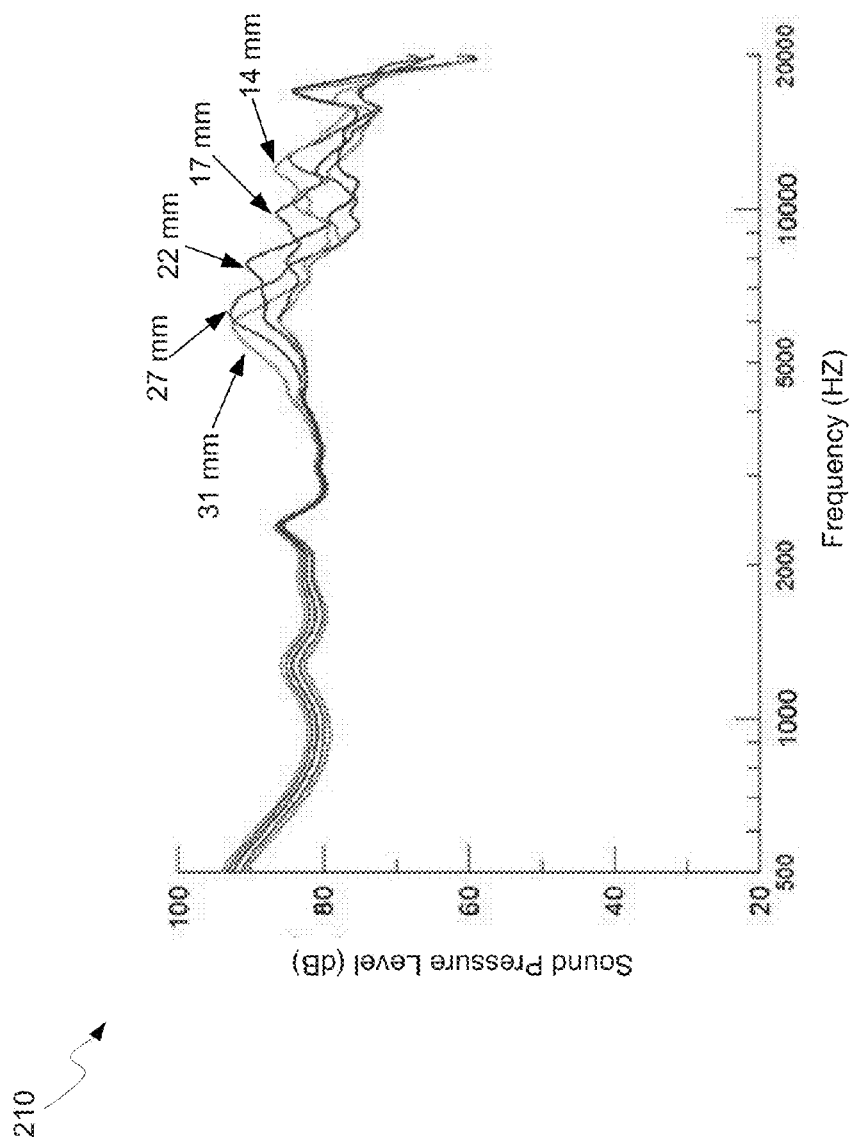
FIG. 2B is a graph of measured eardrum response versus frequency for several different ear tip depths, measured on a human subject.

FIG. 2B is a graph of measured eardrum response versus frequency for several different ear tip depths, measured on a human subject.

FIG. 2A and FIG. 2B show one problem with the prior art. As shown by the response difference shown in FIG. 2A and FIG. 2B, a large variation in stimulus level can occur, because different audiologists may place the ear tip at different depths or the same audiologist may place the ear tip at different depths at different times. For example, the threshold measurement where a subject indicates that a sound is heard may vary significantly with ear tip depth, as illustrated in those figures.

Referring to FIG. 2B, there is shown sound pressure level plot 210 comprising pressure measurements versus frequency for various distances between the probe and the eardrum, as indicated by the distances of 14-31 mm in the plot. These experimental results show the degree to which the pressure of the F1 and F2 tones at the eardrum may vary in the absence of using, for example, forward pressure calibration of the probe.

One recent improvement came from placing a probe microphone in the ear canal, which allows for "forward pressure" calibration. With forward pressure calibration, the eardrum pressure may be made nearly independent of the ear tip placement, so the effect of ear tip placement may be reduced to a few dB instead of the 13 dB illustrated in FIG. 2A. In addition, the microphone in the ear canal may be used to monitor noise levels in the ear canal, providing a warning when the noise is too high to provide good threshold measurements.

Figure 3:
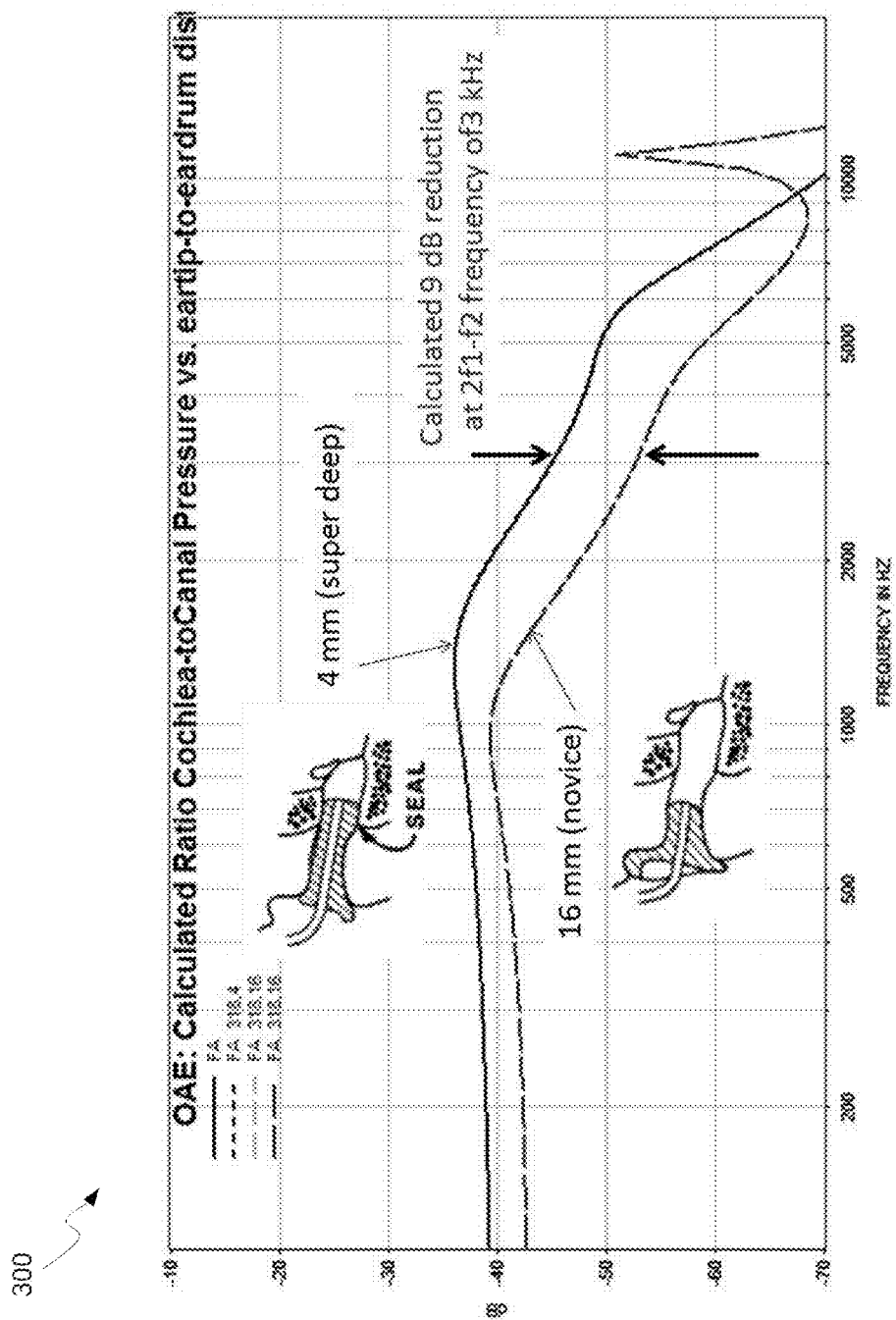
FIG. 3 illustrates calculated cochlea to canal pressure versus frequency for two ear tip to eardrum distances with constant eardrum pressure.

FIG. 3 illustrates calculated cochlea to canal pressure versus frequency for two ear tip to eardrum distances with constant eardrum pressure. Referring to FIG. 3, there is shown calculated cochlea-to-canal pressure ratio 300 for two ear tip-to-ear drum distances with forward pressure calibration. As shown, the plot 300 illustrates another problem with conventional techniques, namely that large variations in the pressure of an otoacoustic emission (OAE) measured in the ear canal at the probe microphone location may result with varying ear tip location even when the pressures of the F1 and F2 tones at the eardrum are held constant using, for example, forward pressure calibration of the probe.

The variation in measured OAE with depth comes about because the sound pressure developed in the ear canal by the OAE emission decreases as the ear canal volume increases. One estimate of the magnitude of this problem is shown in FIG. 3, which shows a calculated 9 dB reduction of OAE at 3 kHz as the ear tip is moved from 4 mm to 16 mm from the eardrum.

The 9 dB reduction shown in FIG. 3 was calculated assuming the effective levels of the stimulus or stimuli at the ear drum have been corrected for the variability shown in FIG. 2. The combined variability with ear tip insertion depth of stimuli pressure and resulting OAE pressure have presented an impediment to the use of OAEs for noise-damage monitoring and ototoxic drug monitoring.

Figure 4:
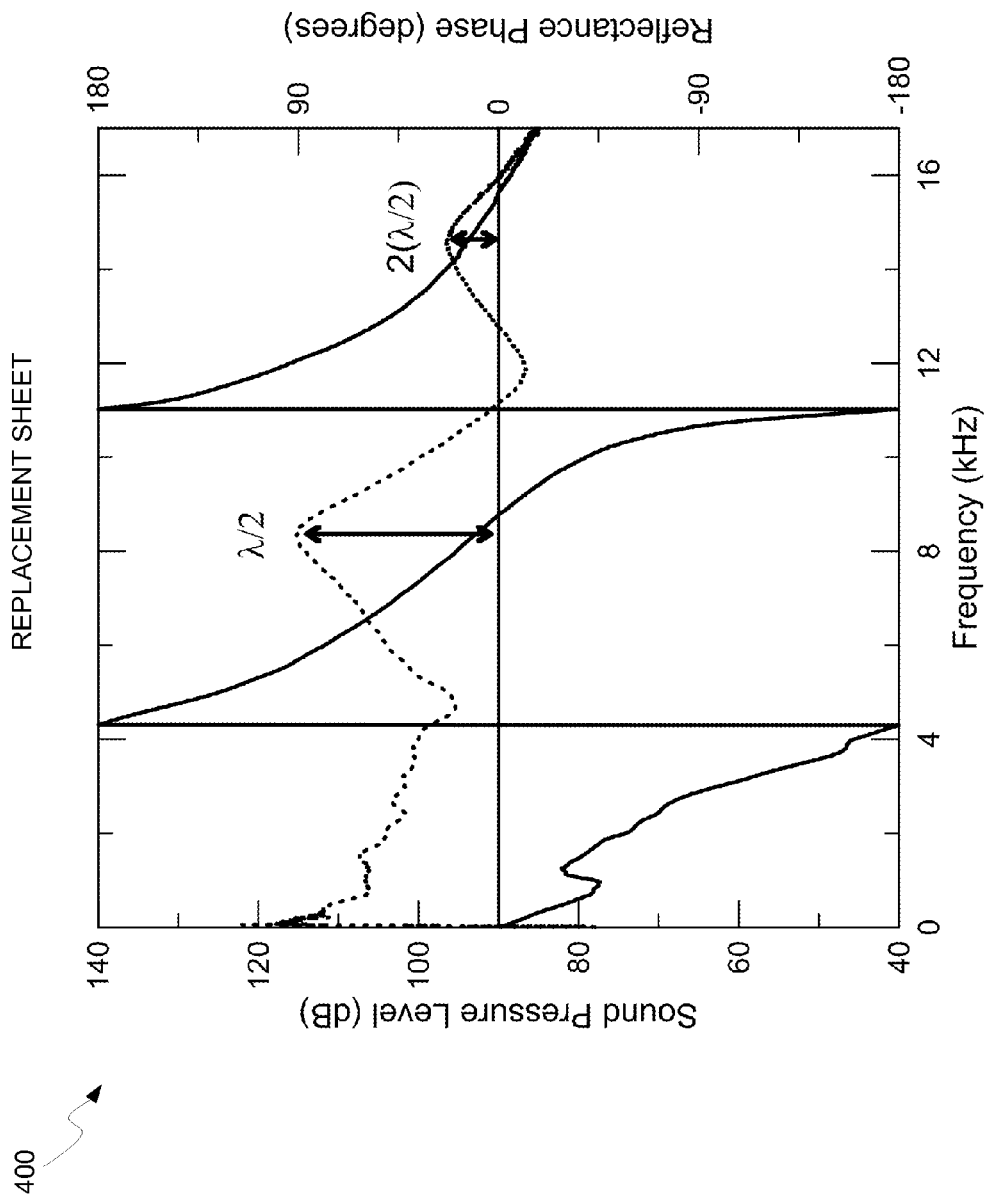
FIG. 4 illustrates sound pressure level and reflectance phase measurements, in accordance with an example embodiment of the disclosure.

FIG. 4 illustrates sound pressure level and reflectance phase measurements, in accordance with an example embodiment of the disclosure. Referring to FIG. 4, there is shown a plot 400 of measured sound pressure and reflectance phase. The sound pressure measurement may comprise identifying the resonance frequency directly as a peak in the pressure. First, the pressure frequency response may be measured using broadband excitation and Fourier analysis. Then, a peak-picking algorithm may be utilized to find a maximum in pressure in the expected range of the resonance.

For the reflectance phase method, reflectance in the ear may be measured using a probe with known Thévenin Source characteristics: source impedance and pressure. The reflectance phase may be extracted as described by Souza (Souza, N., Dhar, S., Neely, S. T and Siegel, J. H. "Comparison of nine methods to estimate ear-canal stimulus levels." J. Acoust. Soc. Am.—press, 2014). Smoothing may be applied if necessary, followed by determining the frequency where total phase accumulation becomes one period. As shown in the example plots of FIG. 4, the first half-wave resonance frequency is approximately 8 kHz by both peak pressure and phase reflectance. For ear tip depths where the half wave resonance exceeds the bandwidth of the system, the fact that the phase is approximately linear with depth at a given frequency can be used to estimate depth.

It is important to note that the value of the depth determination described here does not depend on its absolute accuracy but only on its repeatability in each individual ear. Any errors in the accuracy of the probe to ear drum distance estimate in an individual case are unique to that individual, whether a result of an unusual ear canal shape, unusual ear drum impedance, or the like. An important feature of the present disclosure is that the same meter reading will nearly always produce the same location in the same ear canal, even if the absolute distance measurement contains error.

Figure 5:
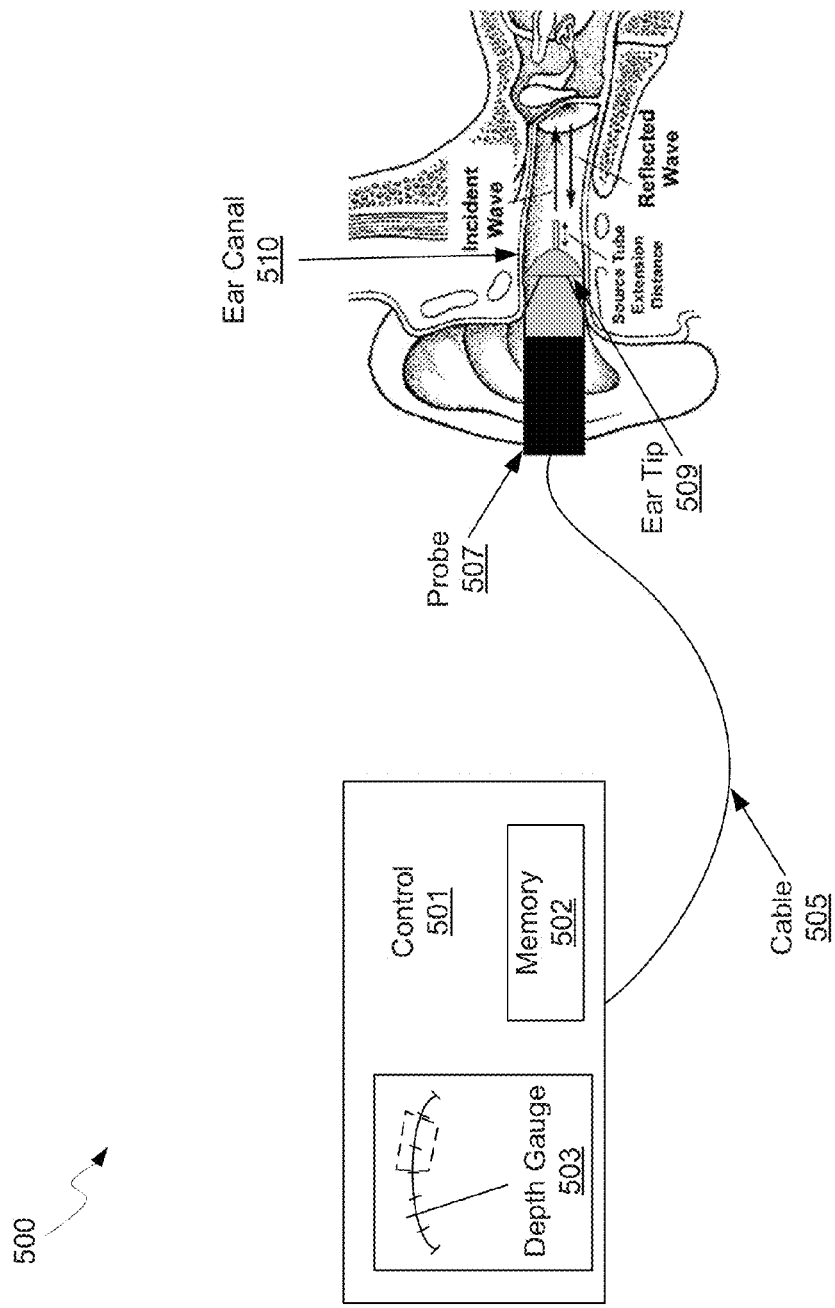
FIG. 5 is a diagram illustrating an example hearing test system with ear tip depth sensing, in accordance with an example embodiment of the disclosure.

FIG. 5 is a diagram illustrating an example hearing test system with ear tip depth sensing, in accordance with an example embodiment of the disclosure. Referring to FIG. 5, there is shown a hearing test system comprising a control system 501 and a probe 507 coupled via a cable 505. The control system 501 may comprise driving circuitry for sound generation circuitry in the probe 507, receiving circuitry for receiving signals from the probe 507, and a depth gauge 503 for accurately positioning the ear tip 509 in the subject ear. In addition, the control system 501 may comprise one or more processors for controlling functions within the control system 501 and the probe 507, and for processing received data, for example. The control system 501 may also comprise a memory 502 for storing determined probe depths, or other information relating to the measurement. Storing the measured depth, as well as other data relevant to the measurement, in memory 502 may enable subsequent measurements to be made at the same depth.

Hearing tests can be sensitive to a number of variables, such as ambient noise, probe seal, ear canal irregularities, and probe ear tip depth. Some measurements are quite sensitive to the ear tip depth, while others may be largely independent.

In an example scenario, an acoustic measurement probe may be placed sealingly into the ear canal, the probe including a source of sound and a microphone to measure the amplitude and phase of the sound pressure produced in the ear canal by the source of sound, with circuitry for measuring the half-wave resonance of an ear canal and/or the frequency at which the phase shift of the reflectance has reached 360 degrees relative to the low-frequency phase and estimating from one or both measurements the distance between the probe tip and the ear drum. This distance may be referred to as the depth of the probe. The determined distance, or depth, may be stored in the memory 502 in the control system 501.

A simple display of that distance may be presented to the person testing the ear, who may thus be guided to place the probe at a suitable depth during initial testing and, more importantly, be guided to place the probe at the same depth for each subsequent test, with the overall result of improved test-retest reliability.

In turn, the increased reliability allows more sensitive comparison between successive tests of the ear in order to provide earlier indication of possible permanent hearing loss as a result of continued exposure to noise. There are now good solutions to the variability of OAE levels with depth due to variations in the stimulus levels at the eardrum, a problem illustrated by the calculation in FIG. 2A and the measured data in FIG. 2B. The hitherto unsolved problem illustrated in FIG. 3 was that even with constant stimulus level at the eardrum, the OAE signal measured by the probe still depends on insertion depth. Both calculations and published data suggest that there may be as much as a one dB change in measured OAE level per mm change in depth. Aspects of the present invention provide a simple, practical method of feedback for the person placing the probe in the ear to allow consistent placement from time to time. With this improvement, the level of the OAE may be practically used to warn of impending permanent hearing loss as discussed below.

Figure 6:
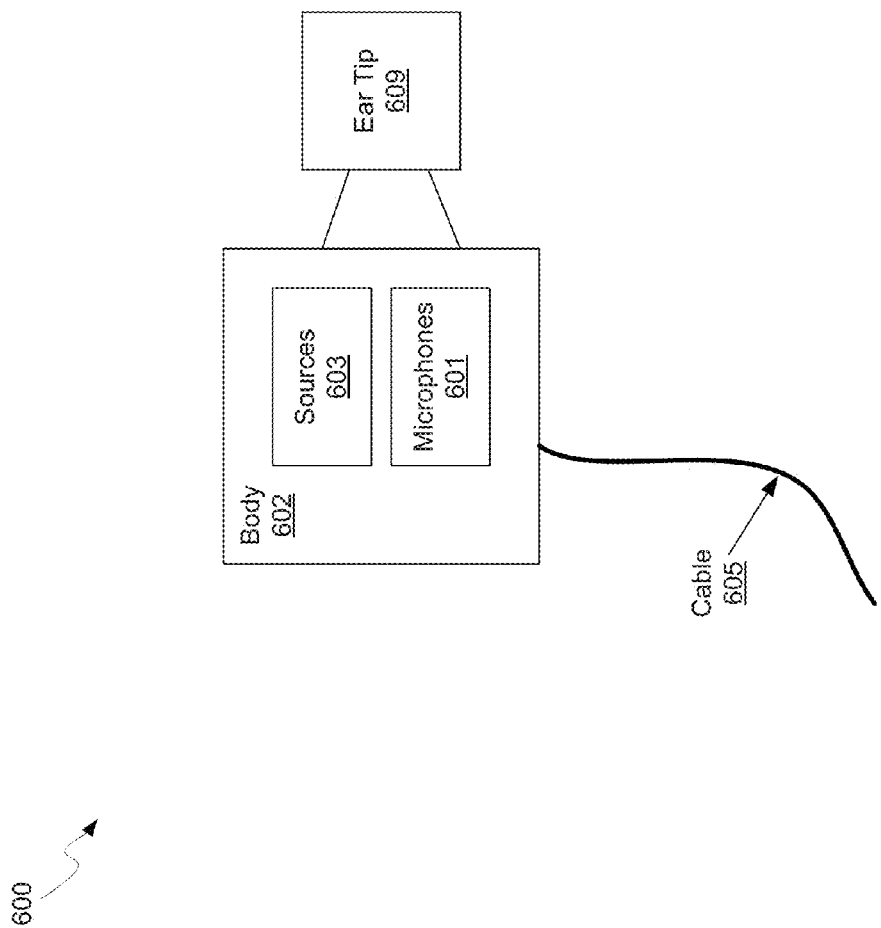
FIG. 6 illustrates an example probe for ear canal assessment, in accordance with an example embodiment of the disclosure.

FIG. 6 illustrates an example probe for ear canal assessment, in accordance with an example embodiment of the disclosure. Referring to FIG. 6, there is shown a probe 607 comprising a body 603, a cable 605, and an ear tip 609. The body 602 may house devices and/or electronics utilized for generating and receiving acoustic signals. For example, the body 602 may house transducers, such as microphones 601 and sources 603, for sensing and generating signals. The sources 603 may comprise miniature loudspeakers, also known historically as receivers.

Figure 7:
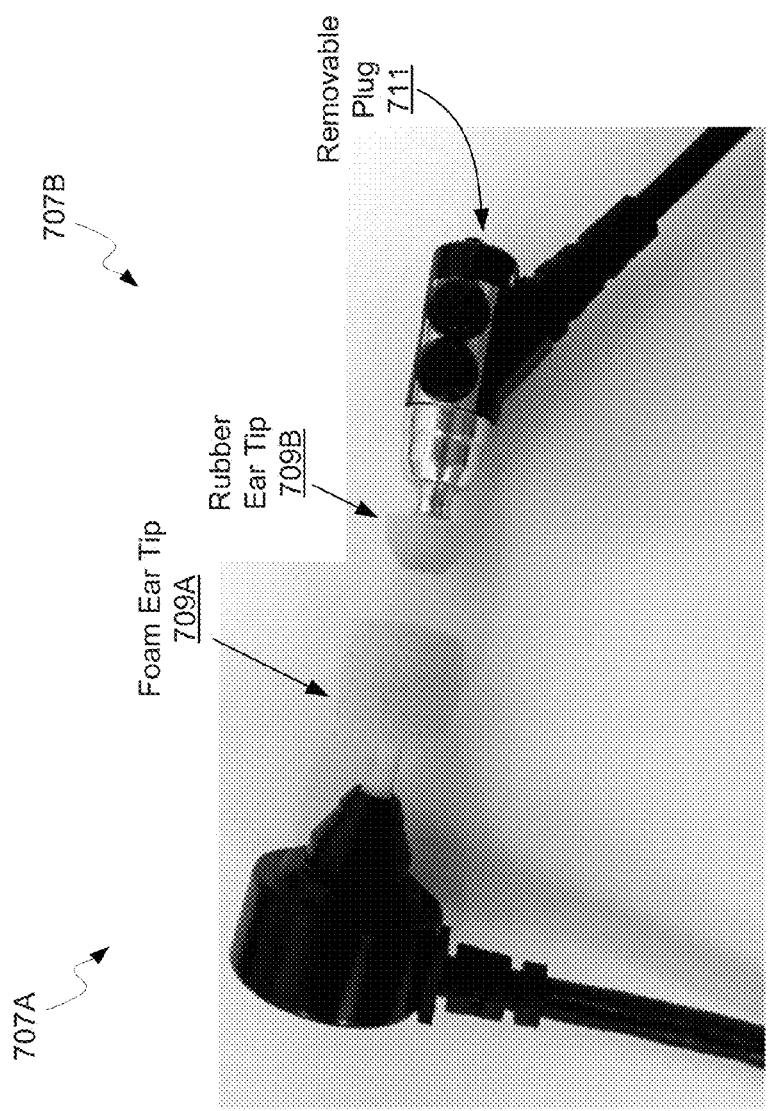
FIG. 7 illustrates example ear probes, in accordance with an example embodiment of the disclosure.

FIG. 7 illustrates example ear probes, in accordance with an example embodiment of the disclosure. Referring to FIG. 7, 707A is an earlier Etymotic Research ER10C probe, and 707B is a new Etymotic Research "10X" probe described in patent application Ser. No. 13/357,184 filed Jan. 24, 2012, Hearing Test Probe Apparatus. For sake of illustration, ear probe 707A is shown with a foam ear tip 709A and probe 707B is shown with a rubber ear tip 709B and removable plug 711. The ear probes 707A and 707B may comprise sound sources and microphones for generating and receiving acoustic signals in an ear canal.

As described in the above patent application, the 10X probe 707B includes a removable plug 711 which exposes a 1.07 mm through hole which permits a 1 mm outer diameter optical borescope to be inserted so a precision optical measurement can be made of the distance from the ear tip to the eardrum. This measurement could be used to display the distance on a meter or other display means, but its likely initial use is in refining and calibrating the magnitude and/or phase measurements described above.

Because various measurements are probe depth dependent, and a proper seal of the probe to the ear canal is also of importance in many measurements, different materials may be used on the probe tip, as illustrated by the foam ear tip 709A and rubber ear tip 709B. The probes 707A and 707B may comprise shielded cables for coupling to control electronics, such as the control system 501 in FIG. 5.

Figure 8:
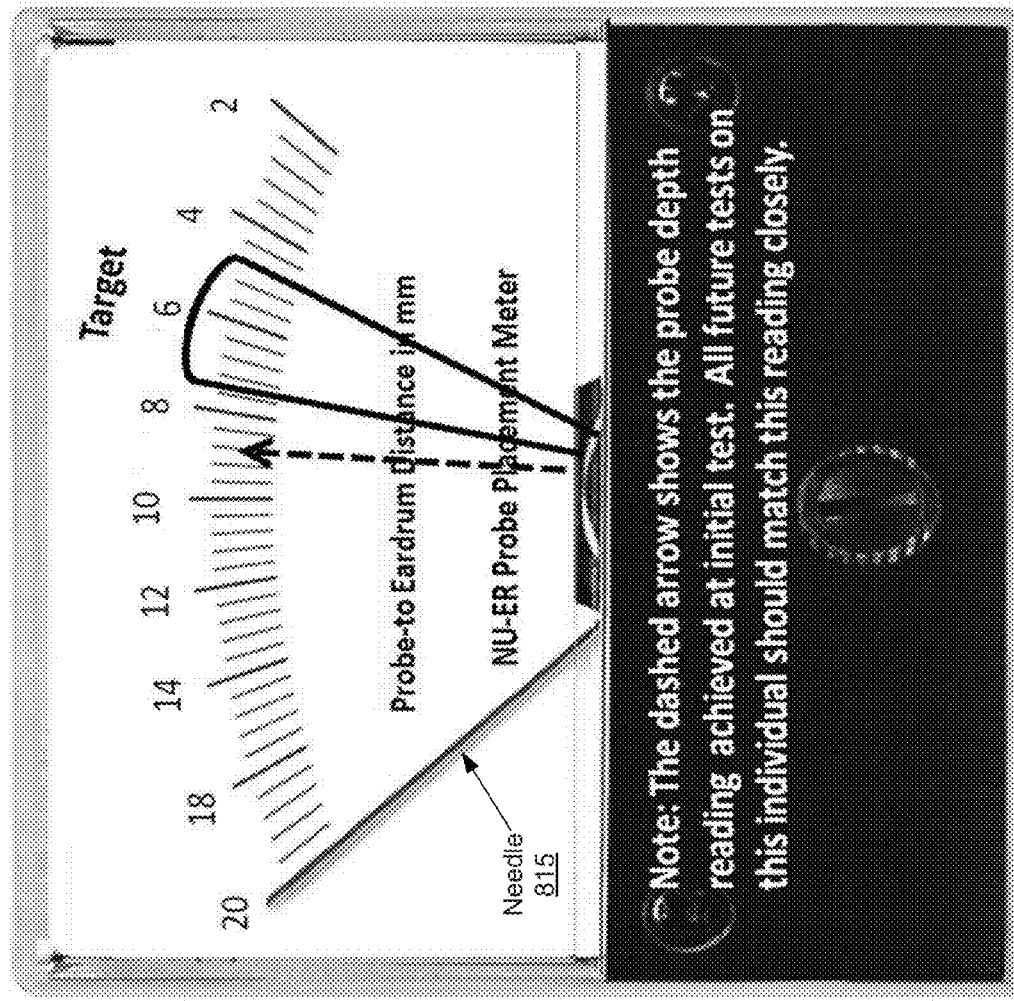
FIG. 8 illustrates an ear tip depth gauge, in accordance with an example embodiment of the disclosure.

FIG. 8 illustrates an ear tip depth gauge, in accordance with an example embodiment of the disclosure. Referring to FIG. 8, there is shown an ear tip depth gauge 803 with an indicator dial with depth, in millimeters, for example, and an indicator needle 815. The dashed arrow shows the probe depth reading achieved at initial test. For accurate and reproducible hearing assessments, subsequent tests are performed at the same depth. It should be noted that while an analog gauge is shown in FIG. 8, the disclosure is not so limited as a digital display or LED indicators may be used, for example.

Insertion depth may be estimated two ways. The first estimate may be obtained by measuring the frequency of the first half-wave resonance of the ear canal pressure, as illustrated in FIG. 4. The second estimate may be obtained by measuring the phase of the reflectance, also shown in FIG. 4. In practice, both methods may be used in combination or separately. The reflectance phase method may be particularly useful when the ear tip is placed so deeply that the half wave resonance frequency is above the upper cutoff frequency of the measurement system.

In order to use the resonance peak detection method, a probe calibration step may be performed to more reliably identify and measure the canal resonances, where the probe 507 shown in FIG. 5 (or probes 707A or 707B in FIG. 7) may be inserted in a long tube, 50 ft. long with an internal diameter of 7.9 mm ($5/16$ inch), approximately the same as that of the average adult human ear, for example, thereby simulating an infinite transmission line, as there would be no reflections due to the loss of acoustic energy over distance. The loss of acoustic energy over distance leaves no measurable reflections from the distal end of this tube. In an example embodiment, a constant voltage signal may be swept from 20 to 20,000 Hz, with a microphone in the probe 107 recording the transmitted signal. This pressure measurement in the tube may thus represent the system's response in an infinite transmission line with a characteristic impedance similar to the average adult ear canal. Therefore, contributions of irregularities in the frequency responses of the sound sources and the microphones in the probe 507 may be compensated for by normalizing subsequent real ear measurements to this calibration scan.

The reflectance phase method of estimating the ear tip placement is described as follows. The phase difference between forward and reflected waves at a given frequency is proportional to the distance from the probe to the ear drum, and may be used to estimate probe position near the ear drum when the half wave resonance is beyond the measurement bandwidth of the system. When the half wave resonance can be measured, the combination of the half wave frequency and the phase shift may both be used to provide even greater accuracy than provided by either one alone. The reflectance phase may rotate through approximately one period from zero frequency to the first half-wave resonance in the canal pressure.

The two methods of determining half-wave resonances described above are illustrated by the plot in FIG. 4. Once the depth has been determined and stored for subsequent tests, reflectance measurements, both magnitude and phase, may be made, which may enable an assessment of the shape of the ear canal. By measuring from the same depth each time, subsequent measurements may be used to determine any changes that may have occurred to the ear canal.

An advantage of the depth measurement described above is that the stimulus levels can now be delivered to the cochlea without the depth dependence of the stimulus shown in FIG. 2A and FIG. 2B. Among other things, forward pressure calibration allows the delivered stimulus to be held nearly constant with changes in the depth of the probe. By utilizing the depth meter 803, the variability with depth of OAE pressure measured at the probe microphone location may be minimized by minimizing test/retest differences in depth, a problem illustrated by the calculation in FIG. 3, and by published research, both suggesting it can cause up to 1 dB change in measured OAE level for each mm change in depth. The depth meter 803 provides a simple, practical method of feedback for the person placing the probe in the ear to encourage deeper placement.

As discussed above, whatever the absolute accuracy of the distance to eardrum determination and whatever the errors in an individual case, those errors will generally be unique to and fixed for that individual. The distance estimate will change, however, if the shape of the ear canal changes. This might happen from a buildup of earwax, or more rarely, ear canal swelling from infection, or from surgery. Any of those conditions would be visible to the clinician during an otoscopic examination, which are considered standard practice before inserting a probe or other ear tip into the ear canal. Otherwise, the same meter reading will nearly always correspond to the same location in the ear canal.

In an embodiment of the disclosure, a method and system may comprise in a hearing assessment system comprising a control system and a probe with a sealing ear tip, a microphone, and a sound source: measuring ear canal pressure versus frequency of an ear canal, calculating a reflectance from the measured ear canal pressure versus frequency, and calculating a distance between the hearing probe and an eardrum in the ear canal based on a phase versus frequency extracted from the calculated reflectance.

In another embodiment of the disclosure, a method may comprise in a hearing assessment system comprising a control system and a probe with a sealing ear tip, a microphone, and a sound source: measuring a pressure versus frequency in an ear canal, determining a first half-wavelength frequency of the ear canal using the measured pressure versus frequency, and calculating a distance between the hearing probe and an eardrum in the ear canal based on the determined first half-wavelength frequency.

The distance between the hearing probe and the ear drum in the ear canal may be calculated utilizing a phase versus frequency extracted from a reflectance calculated from the measured pressure versus frequency in conjunction with the determined first half-wavelength frequency.

In another embodiment of the disclosure, a system may comprise a hearing probe comprising a sealing ear tip, a microphone, and a sound source; and a control system for controlling the hearing probe, the system being operable to: measure ear canal pressure versus frequency of an ear canal; calculate a reflectance from the measured ear canal pressure versus. frequency; and calculate a distance between the hearing probe and an eardrum in the ear canal based on a phase versus frequency extracted from the calculated reflectance.

Subsequent measurements in the ear canal may be performed using the calculated distance. The calculated distance may be stored in a memory in the control system for the subsequent measurements in the ear canal. The calculated distance may be displayed on a gauge on the control system. The distance between the hearing probe and the eardrum in the ear canal may be calculated utilizing a measured pressure versus frequency in conjunction with the extracted phase versus frequency.

In another example embodiment, a method may comprise in a hearing assessment system comprising a control system and a probe with a sealing ear tip, a microphone, and a sound source: measuring a pressure versus frequency of an ear canal, determining a first half-wavelength frequency of the ear canal using the measured pressure versus frequency, and calculating a distance between the hearing probe and an eardrum in the ear canal based on the determined first half-wavelength frequency.

Other embodiments may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the steps as described herein for rapidly determining and displaying the depth of ear tip placement to improve the reliability of hearing tests.

Accordingly, aspects of the invention may be realized in hardware, software, firmware or a combination thereof. The invention may be realized in a centralized fashion in at least one computer system or in a distributed fashion where different elements are spread across several interconnected computer systems. Any kind of computer system or other apparatus adapted for carrying out the methods described herein is suited. A typical combination of hardware, software and firmware may be a general-purpose computer system with a computer program that, when being loaded and executed, controls the computer system such that it carries out the methods described herein.

One embodiment may be implemented as a board level product, as a single chip, application specific integrated circuit (ASIC), or with varying levels integrated on a single chip with other portions of the system as separate components. The degree of integration of the system will primarily be determined by speed and cost considerations. Because of the sophisticated nature of modern processors, it is possible to utilize a commercially available processor, which may be implemented external to an ASIC implementation of the present system. Alternatively, if the processor is available as an ASIC core or logic block, then the commercially available processor may be implemented as part of an ASIC device with various functions implemented as firmware.

The present invention may also be embedded in a computer program product, which comprises all the features enabling the implementation of the methods described herein, and which when loaded in a computer system is able to carry out these methods. Computer program in the present context may mean, for example, any expression, in any language, code or notation, of a set of instructions intended to cause a system having an information processing capability to perform a particular function either directly or after either or both of the following: a) conversion to another language, code or notation; b) reproduction in a different material form. However, other meanings of computer program within the understanding of those skilled in the art are also contemplated by the present invention.

While the invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims.

What is claimed is:

1. A system for assessing hearing, the system comprising:
    a hearing probe comprising a sealing ear tip, a microphone, and a sound source;
    a control system for controlling the hearing probe, said system being operable to:
        measure a pressure versus frequency of an ear canal;
        determine a first half-wavelength frequency of the ear canal using the measured ear canal pressure versus frequency; and
        calculate a first distance between the hearing probe and an eardrum in the ear canal based on the determined first half-wavelength frequency; and
    a display configured to present visual feedback for positioning the hearing probe, the visual feedback providing the calculated first distance between the hearing probe and the eardrum in the ear canal.

2. The system according to claim 1, comprising a memory configured to store a previously calculated second distance between the hearing probe and the eardrum of a same patient corresponding with a prior measurement, and wherein the visual feedback presented at the display provides the calculated first distance and the previously calculated second distance.

3. The system according to claim 1, comprising a memory configured to store the calculated first distance, and wherein the calculated first distance is presented at the display for subsequent measurements in the ear canal of a same patient.

4. The system according to claim 1, wherein the display configured to present the visual feedback providing the calculated first distance comprises a gauge on the control system.

5. The system according to claim 1, wherein a phase versus frequency extracted from a reflectance calculated from the measured ear canal pressure versus frequency is also used to calculate the first distance between the hearing probe and the eardrum in the ear canal.

6. A method for assessing hearing, the method comprising:
    in a hearing assessment system comprising a control system, a display, and a probe with a sealing ear tip, a microphone, and a sound source:
        measuring a pressure versus frequency of an ear canal;
        determining a first half-wavelength frequency of the ear canal using the measured pressure versus frequency;
        calculating a first distance between the hearing probe and an eardrum in the ear canal based on the determined first half-wavelength frequency; and
        presenting, at the display, visual feedback for positioning the hearing probe, the visual feedback providing the calculated first distance between the hearing probe and the eardrum in the ear canal.

7. The method according to claim 6, comprising storing in a memory a previously calculated second distance between the hearing probe and the eardrum of a same patient corresponding with a prior measurement, wherein the visual feedback presented at the display provides the calculated first distance and the previously calculated second distance.

8. The method according to claim 6, comprising storing the calculated first distance in a memory, and wherein the calculated first distance is presented at the display for subsequent measurements in the ear canal.

9. The method according to claim 6, wherein the visual feedback providing the calculated first distance is presented at the display comprising a gauge on the control system.

10. The method according to claim 6, comprising calculating the first distance between the hearing probe and the ear drum in the ear canal utilizing a phase versus frequency extracted from a reflectance calculated from the measured pressure versus frequency in conjunction with the determined first half-wavelength frequency.

11. A system for assessing hearing, the system comprising:
    a hearing probe comprising a sealing ear tip, a microphone, and a sound source;
    a control system for controlling the hearing probe, said system being operable to:
        measure ear canal pressure versus frequency of an ear canal;
        calculate a reflectance from the measured ear canal pressure versus frequency; and
        calculate a first distance between the hearing probe and an eardrum in the ear canal based on a phase versus frequency extracted from the calculated reflectance; and
    a display configured to present visual feedback for positioning the hearing probe, the visual feedback providing the calculated first distance between the hearing probe and the eardrum in the ear canal.

12. The system according to claim 11, comprising a memory configured to store a previously calculated second distance between the hearing probe and the eardrum of a same patient corresponding with a prior measurement, and wherein the visual feedback presented at the display provides the calculated first distance and the previously calculated second distance.

13. The system according to claim 11, comprising a memory configured to store the calculated first distance, and wherein the calculated first distance is presented at the display for subsequent measurements in the ear canal of a same patient.

14. The system according to claim 11, wherein the display configured to present the visual feedback providing the calculated first distance comprises a gauge on the control system.

15. The system according to claim 11, wherein a pressure versus frequency of the ear canal is also used to calculate the first distance between the hearing probe and the eardrum in the ear canal.

16. A method for assessing hearing, the method comprising:
in a hearing assessment system comprising a control system, a display, and a probe with a sealing ear tip, a microphone, and a sound source:
measuring ear canal pressure versus frequency of an ear canal;
calculating a reflectance from the measured ear canal pressure versus frequency;
calculating a first distance between the hearing probe and an eardrum in the ear canal based on a phase versus frequency extracted from the calculated reflectance; and
presenting, at the display, visual feedback for positioning the hearing probe, the visual feedback providing the calculated first distance between the hearing probe and the eardrum in the ear canal.

17. The method according to claim 16, comprising storing in a memory a previously calculated second distance between the hearing probe and the eardrum of a same patient corresponding with a prior measurement, wherein the visual feedback presented at the display provides the calculated first distance and the previously calculated second distance.

18. The method according to claim 16, comprising storing the calculated first distance in a memory, and wherein the calculated first distance is presented at the display for subsequent measurements in the ear canal.

19. The method according to claim 16, wherein the visual feedback providing the calculated first distance is presented at the display comprising a gauge on the control system.

20. The method according to claim 16, comprising calculating the first distance between the hearing probe and the eardrum in the ear canal utilizing a measured pressure versus frequency in conjunction with the extracted phase versus frequency.

* * * * *